US011779921B2

(12) United States Patent
Bordy et al.

(10) Patent No.: US 11,779,921 B2
(45) Date of Patent: Oct. 10, 2023

(54) MICROFLUIDIC DEVICE FOR PREPARING AND ANALYZING A BIOLOGICAL SAMPLE

(71) Applicant: Commissariat a l'Energie Atomique et aux Energies Alternatives, Paris (FR)

(72) Inventors: Thomas Bordy, Grenoble (FR); Anne-Gaelle Bourdat, Grenoble (FR); Remi Toutain, Grenoble (FR); Caroline Paulus, Grenoble (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 496 days.

(21) Appl. No.: 16/930,882

(22) Filed: Jul. 16, 2020

(65) Prior Publication Data
US 2021/0016282 A1 Jan. 21, 2021

(30) Foreign Application Priority Data
Jul. 17, 2019 (FR) ...................... 19 08032

(51) Int. Cl.
*C12Q 1/686* (2018.01)
*B01L 3/00* (2006.01)
*C12M 3/06* (2006.01)

(52) U.S. Cl.
CPC ....... *B01L 3/502753* (2013.01); *C12M 23/16* (2013.01); *C12Q 1/686* (2013.01);
(Continued)

(58) Field of Classification Search
CPC ......... B01L 3/502753; B01L 2300/044; B01L 2200/027; B01L 2200/0621;
(Continued)

(56) References Cited

U.S. PATENT DOCUMENTS

2002/0124896 A1 9/2002 O'Connor et al.
2009/0038417 A1 2/2009 Lee
(Continued)

FOREIGN PATENT DOCUMENTS

EP 3 222 989 B1 8/2018

OTHER PUBLICATIONS

French Preliminary Search Report dated Mar. 16, 2020 in French Application 19 08032 filed Jul. 17, 2019 (with English Translation of Categories of Cited Documents and Written Opinion), 13 pages.

*Primary Examiner* — Young J Kim
(74) *Attorney, Agent, or Firm* — Oblon, McClelland, Maier & Neustadt, L.L.P.

(57) ABSTRACT

A microfluidic device includes a single rigid support and a first unit having a first chamber of nonzero volume delimited by walls of the support. A filter separates the first chamber into a first space and a second space, a first channel made in the support and a second channel. The device also includes a second unit including a second chamber, a third channel. The device further includes a first fluidic transfer channel between the first chamber and the second chamber, made in the support and opening on the one hand into said second chamber and on the other hand at a first bypass node in the second channel. The device including first flow switching means arranged for selecting connection of the first chamber to the exterior only, via the second channel only or to the second chamber only, through the first transfer channel.

14 Claims, 12 Drawing Sheets

(52) U.S. Cl.
CPC . *B01L 2200/0689* (2013.01); *B01L 2300/044* (2013.01); *B01L 2300/165* (2013.01)

(58) Field of Classification Search
CPC ..... B01L 2300/0681; B01L 2300/0816; B01L 2300/0861; B01L 3/502715; C12Q 1/686
See application file for complete search history.

(56) References Cited

U.S. PATENT DOCUMENTS

2016/0077062 A1   3/2016  Leckebusch et al.
2017/0268041 A1*  9/2017  Gosselin ................ C12Q 1/686

* cited by examiner

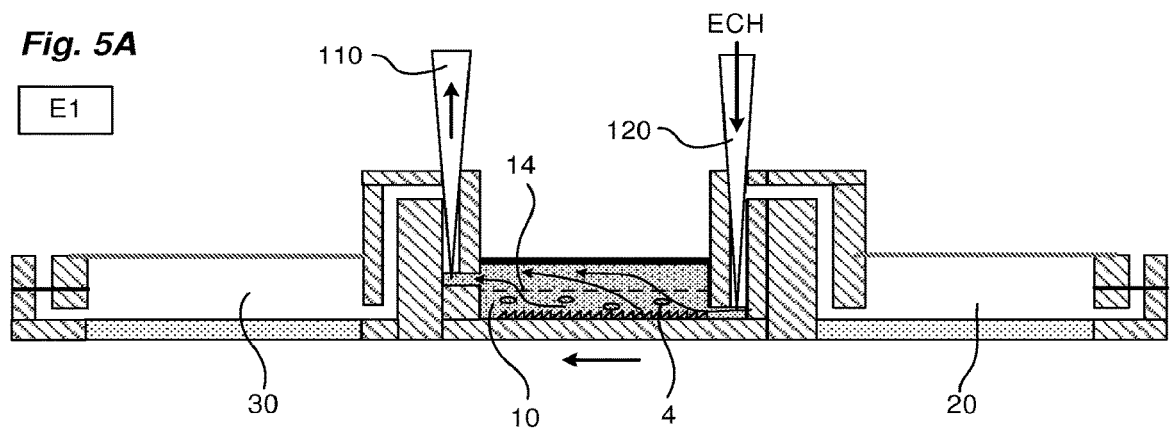
*Fig. 5A*
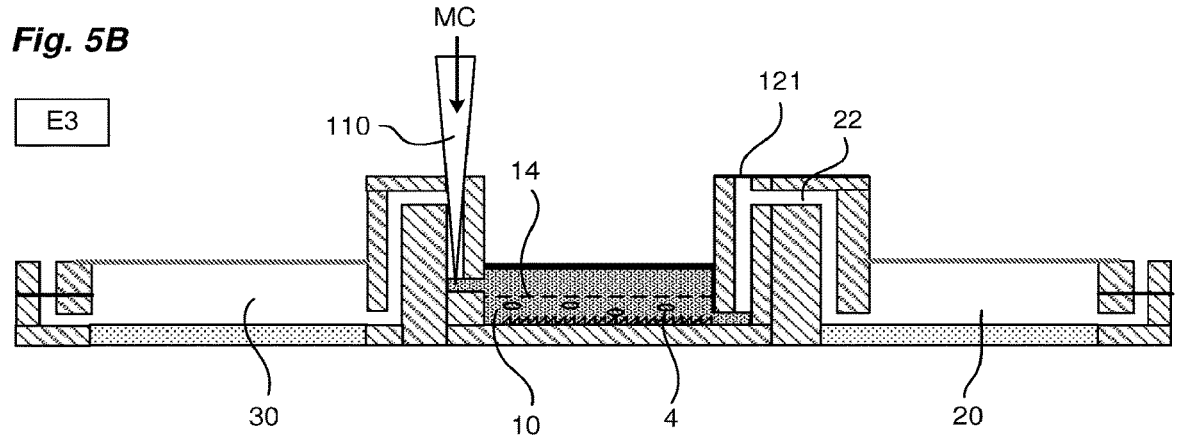
*Fig. 5B*
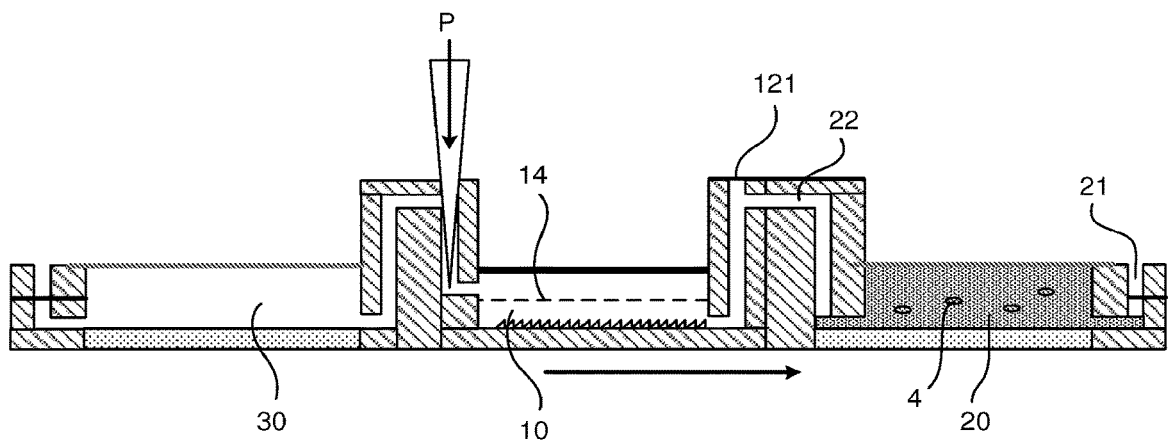

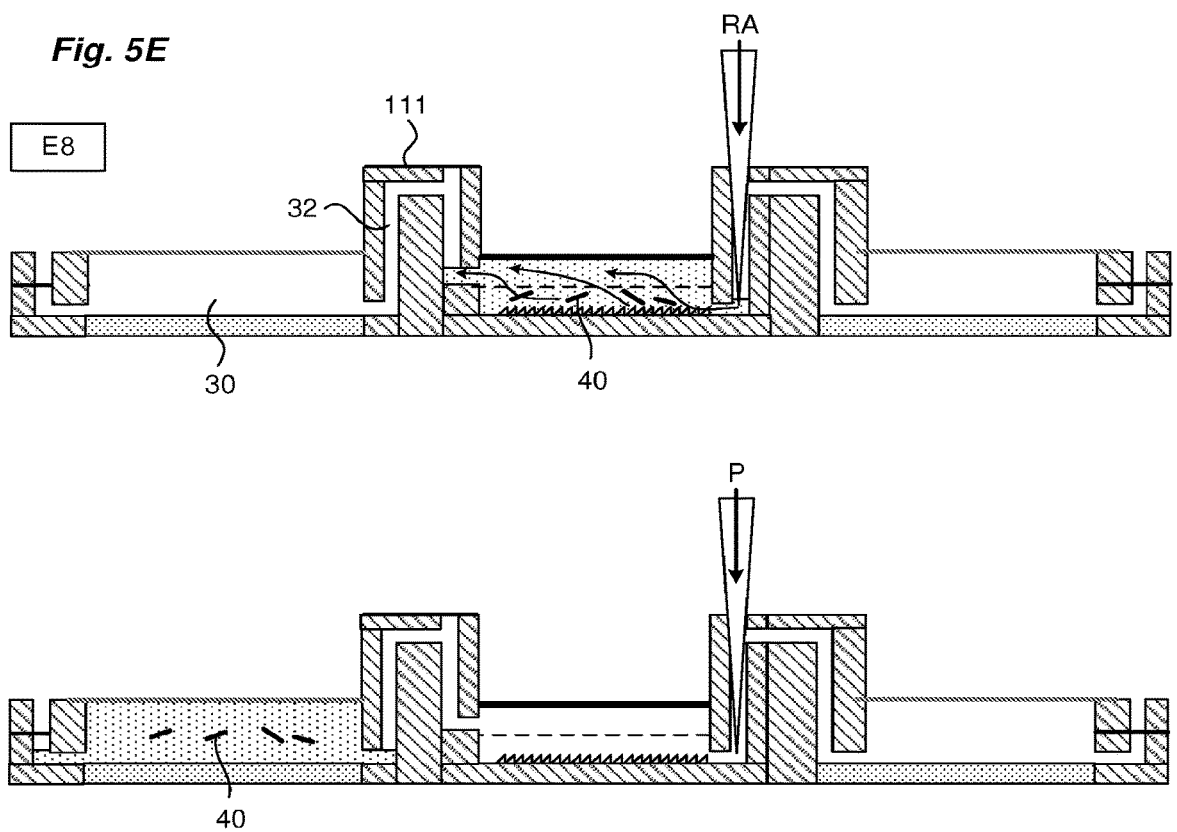
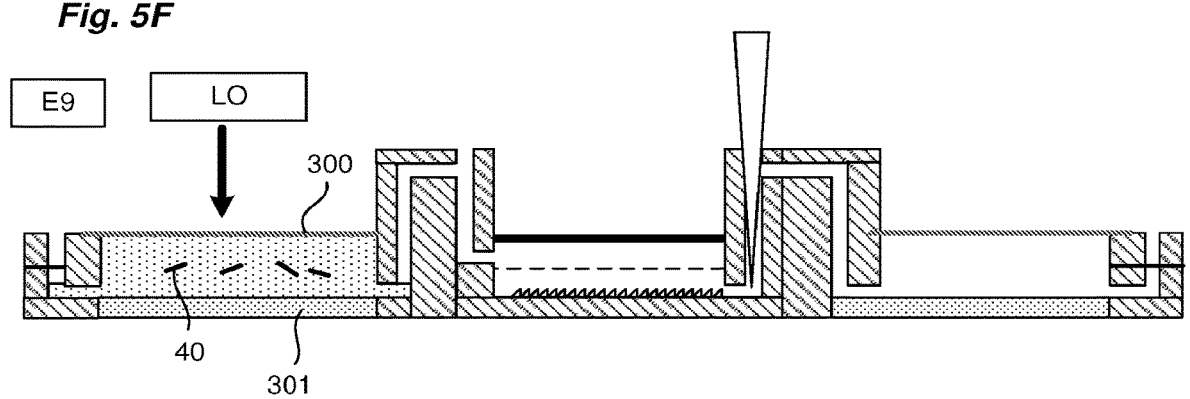

MICROFLUIDIC DEVICE FOR PREPARING AND ANALYZING A BIOLOGICAL SAMPLE

TECHNICAL FIELD OF THE INVENTION

The present invention relates to a microfluidic device for preparing and analyzing a biological sample containing biological species.

This device notably makes it possible to perform all the steps of preparation and analysis of the sample in one and the same rigid support.

PRIOR ART

Since the invention of PCR ("Polymerase Chain Reaction") and of qPCR ("Quantitative PCR"), numerous applications have been developed around molecular biology for detecting and identifying organisms from their nucleic acids. In most cases it is a question of PCR detection using DNA primers specific to a given target (rare cells in the blood, viruses in the respiratory tract or bacteria in food matrices). A step of preamplification by culturing the cells under investigation is often necessary because the test is not always sensitive enough to detect very low concentrations, or the matrix and the cellular (or bacterial, or viral) lysis reagent in which the sample is located is an inhibitor of the test (e.g. blood, cheese etc.). It is then necessary to dilute the sample to decrease the inhibitors, which leads to dilution of the target cells or DNA.

Currently, the known assays are carried out in three main steps: a step of culturing the sample, then lysis of the cells to make the DNA accessible, then a step of purification or dilution of the nucleic acids present and of biomolecular amplification. The culture step is inexpensive but proves to be very long (from 8 h to 72 h). For its part, the step of DNA release and purification/dilution for amplification of the nucleic acids requires numerous manipulations, which makes it difficult to understand by untrained personnel. It can certainly be carried out automatically, but the known equipment is often imposing and expensive.

The detection of pathogens in a biological sample is therefore often carried out in the laboratory using heavy equipment that is unsuitable for rapid analysis in the field. As a reminder, setting up said detection on a biological sample may require all the following steps to be carried out:
  enrichment in a culture medium,
  concentrating the biological species present in the sample,
  purification of the targeted biological species,
  lysis of the biological species contained in the sample to disrupt said species and release biological material to be analyzed,
  purification and/or dilution of the biological material,
  biomolecular amplification of the qPCR, LAMP, RPA type, or any other method of detection by biomolecular amplification or sequencing
  visual detection of the amplification at each cycle such as for example by fluorescence, colorimetry, holographic imaging, turbidimetry, pH measurement in conjunction with the amplification reaction.

Devices that make it possible to carry out some of the steps described above, notably the steps of concentration, purification and mechanical lysis, are known from the prior art. Patent application WO2015/181743A1 notably describes such a device. In the latter, mechanical lysis is carried out by shearing between two walls, one of the two walls having a rough contact surface. Such a device essentially makes it possible to carry out grinding, and is not suitable for implementing a more complete analysis of a biological sample, analysis by visual detection having to be carried out after transferring the sample out of the device, which may lead to contamination of the sample and distort the results.

There are also solutions that make it possible to detect the presence of pathogens by amplification and detection by colorimetry or turbidity. Solutions of this kind are described for example in the following works:
  "*Visual detection of isothermal nucleic acid amplification using pH-sensitive dyes*", Nathan A. Tanner et al.—BioTechniques, Vol. 58, No. 2, February 2015, pp. 59-68.
  "*Colorimetric detection of loop-mediated isothermal amplification reaction by using hydroxy naphthol blue*", Motoki Goto et al.—BioTechniques, Vol. 46, No. 3, March 2009, pp. 167-172.
  "*Loop-Mediated Isothermal Amplification Assay for Rapid Detection of Common Strains of Escherichia coli*", Hill J, Beriwal S, Chandra I, et al.—Journal of Clinical Microbiology. 2008; 46(8):2800-2804. doi: 10.1128/JCM.00152-08.
  "*Visual Detection of Norovirus Genogroup II by Reverse Transcription Loop-Mediated Isothermal Amplification with Hydroxynaphthol Blue Dye*", Jianming, Ziqian Xu, Kai Nie, Xiong Ding, Li Guan, Ji Wang, Yuying Xian, Xiyang Wu, Xuejun Ma—Food and Environmental Virology, September 2014, Volume 6, Issue 3, pp 196-201.

For its part, patent EP3222989B1 describes a microfluidic device that also makes it possible to carry out some of the steps described above, notably concentration, lysis and detection by optical reading.

This last-mentioned device is therefore particularly complete but it does not allow all the steps described above to be carried out. Moreover, even if certain steps may still be optional, it is useful to have a more versatile device at our disposal that makes it possible to carry out all the steps, without transferring the sample out of the device and therefore without risk of contamination.

DISCLOSURE OF THE INVENTION

This versatile microfluidic device thus makes it possible to prepare and analyze a biological sample and comprises:
  a single rigid support,
  a first unit comprising a first chamber of nonzero volume delimited by walls of the support, a filter separating said first chamber into a first space and a second space, a first channel made in said support opening at one end onto a surface of said support and at another end into said first space and a second channel made in said support and opening at one end onto a surface of said support and at another end into said second space,
  a second unit comprising a second chamber made in said rigid support and delimited at least partially by a transparent wall of said support, a third channel made in said support and opening at one end onto a surface of said support and at another end into said second chamber,
  a first channel for fluidic transfer between the first chamber and the second chamber, made in said support and opening on the one hand into said second chamber and on the other hand at a first bypass node into said second channel,
  first flow switching means arranged for selecting connection of the first chamber:

to the exterior only via the second channel only or,
to the second chamber only through the first transfer channel.

According to a particular feature, the first unit comprises a rough contact surface made at the bottom of its first chamber.

According to another particular feature, the first chamber is closed by a deformable membrane.

According to another particular feature, the first unit is configured for carrying out one or more of the following steps of a method for preparing and analyzing a biological sample:
   concentrating the biological species present in a biological sample,
   washing to purify the biological species,
   receiving a culture medium,
   culturing the biological species,
   lysis of the biological species in order to release a biological material,
   separating the biological material.

According to another particular feature, the second unit is configured for carrying out one or more of the following steps of a method for preparing and analyzing a biological sample:
   culturing the biological species,
   visual monitoring of growth during said culture step,
   detecting the presence of pathogens in the separated biological material, by biomolecular amplification.

According to another particular feature, the device comprises a first hydrophobic membrane sealing the third channel.

According to another particular feature, the device comprises:
   a third unit comprising a third chamber made in said rigid support and delimited at least partially by a transparent wall of said support, a fourth channel made in said support and opening at one end onto a surface of said support and at another end into said third chamber.

According to another particular feature, the device comprises:
   a second channel for fluidic transfer between the first chamber (10) and the third chamber, made in said support and opening on the one hand into said third chamber and on the other hand at a second bypass node into said first channel.

According to another particular feature, the device comprises second flow switching means arranged for selecting connection of the first chamber:
   to the exterior only via the first channel only or,
   to the third chamber only through the second transfer channel.

According to another particular feature, the third unit is configured for carrying out the following step of a method for preparing and analyzing a biological sample:
   detecting the presence of pathogens in the separated biological material, by biomolecular amplification.

According to another particular feature, the device comprises a second hydrophobic membrane sealing the fourth channel.

The reaction of the qPCR type consists of an amplification of a target DNA or RNA sequence (representative of one organism in particular) coupled to an intercalator or a probe producing fluorescence detectable by an optical apparatus in the event of amplification of this sequence. Thus, if the level of fluorescence increases during the reaction, this signifies that the amplification reaction takes place and that therefore the DNA or RNA of the target organism was indeed present.

However, in the case of absence of reaction, it is necessary to be able to confirm that this is due to absence of the organism sought and not to inhibition of the amplification reaction, which would give rise to a false negative. The enzymes responsible for the amplification reaction are in fact sensitive to many inhibitors supplied by the sample being analyzed.

In order to guarantee that absence of amplification does indeed signify absence of the target, internal reaction controls are put in place. Most of the time it is another DNA target deliberately added to the test, which will be amplified simultaneously with the sample of interest. It is then necessary to be able to discriminate the two reactions. Several strategies are used industrially:
   One could be to use a portion of the sample for conducting the control in parallel, as an independent reaction. This necessitates fractionating the initial sample, leading to a loss of sensitivity/representativeness of the assay. The advantage is that it is possible to use any technique of detection of amplification for this control (example: fluorescent DNA intercalator).
   To avoid splitting the sample, another strategy consists of conducting the control in the same reaction as the target sequence: for example, using DNA probes specific to the target sequence and in parallel DNA probes specific to the control sequence (with a different fluorochrome for each probe). This solution makes it possible to assay the whole sample but is not compatible with all detection techniques, notably with the use of a nonspecific intercalating agent, of a sequence or of any other nonspecific method of sequence detection (colorimetry, pH measurement etc.).

Patent application EP0586112A2 and patent U.S. Pat. No. 6,312,930B1 each describe a method of detection that makes it possible to eliminate false negatives, by adding a control target.

The invention therefore also aims to endow the second chamber with a particular architecture, by shaping its internal volume.

According to another particular feature, the second chamber thus comprises at least one recess intended to receive a compound for internal reaction control.

According to another particular feature, the second chamber is made of several superposed strata and said recess is made in one of said strata only.

The invention also relates to a method for preparing and analyzing a biological sample containing biological species, said method being carried out using a microfluidic device as defined above, in which:
   the first unit is configured for carrying out one or more of the following steps of said method:
      concentrating the biological species present in a biological sample,
      washing to purify the biological species,
      receiving a culture medium,
      culturing the biological species,
      lysis of the biological species in order to release a biological material,
      separating the biological material,
   the second unit is configured for carrying out one or more of the following steps of said method:
      culturing the biological species,
      visual monitoring of growth during said culture step,
      detecting the presence of pathogens in the separated biological material, by biomolecular amplification,
   the third unit is configured for carrying out the following step of said method:

detecting the presence of pathogens in the separated biological material, by biomolecular amplification.

BRIEF DESCRIPTION OF THE FIGURES

Other features and advantages will be made clear in the detailed description given hereunder, referring to the appended drawings, in which:

FIGS. 5A to 5F show the different steps of preparation and analysis carried out with the device in FIG. 2C.

DETAILED DESCRIPTION OF AT LEAST ONE EMBODIMENT

The microfluidic device of the invention is intended for analyzing a biological sample. This biological sample is for example in the form of a fluid that contains biological species containing a biological material to be investigated.

"Biological species" notably means microorganisms, cells, spores, viruses etc. "Biological material to be investigated" means for example nucleic acid molecules (RNA, DNA) obtained from a cell, proteins, lipopolysaccharides (LPS), lipoteichoic acids (LTA) etc.

"Fluid" notably means a liquid, a gas etc. The liquid may have different degrees of viscosity and for example may be in the form of a paste or a gel.

In the rest of the description, the terms "lower", "upper", "high" and "low" used are to be understood as being with reference to a principal axis (X), which is vertical.

In the rest of the description, the terms "external", "exterior", "internal", "interior", must be understood as being with reference to the chambers of the device, which will be described hereunder.

Figure 1:
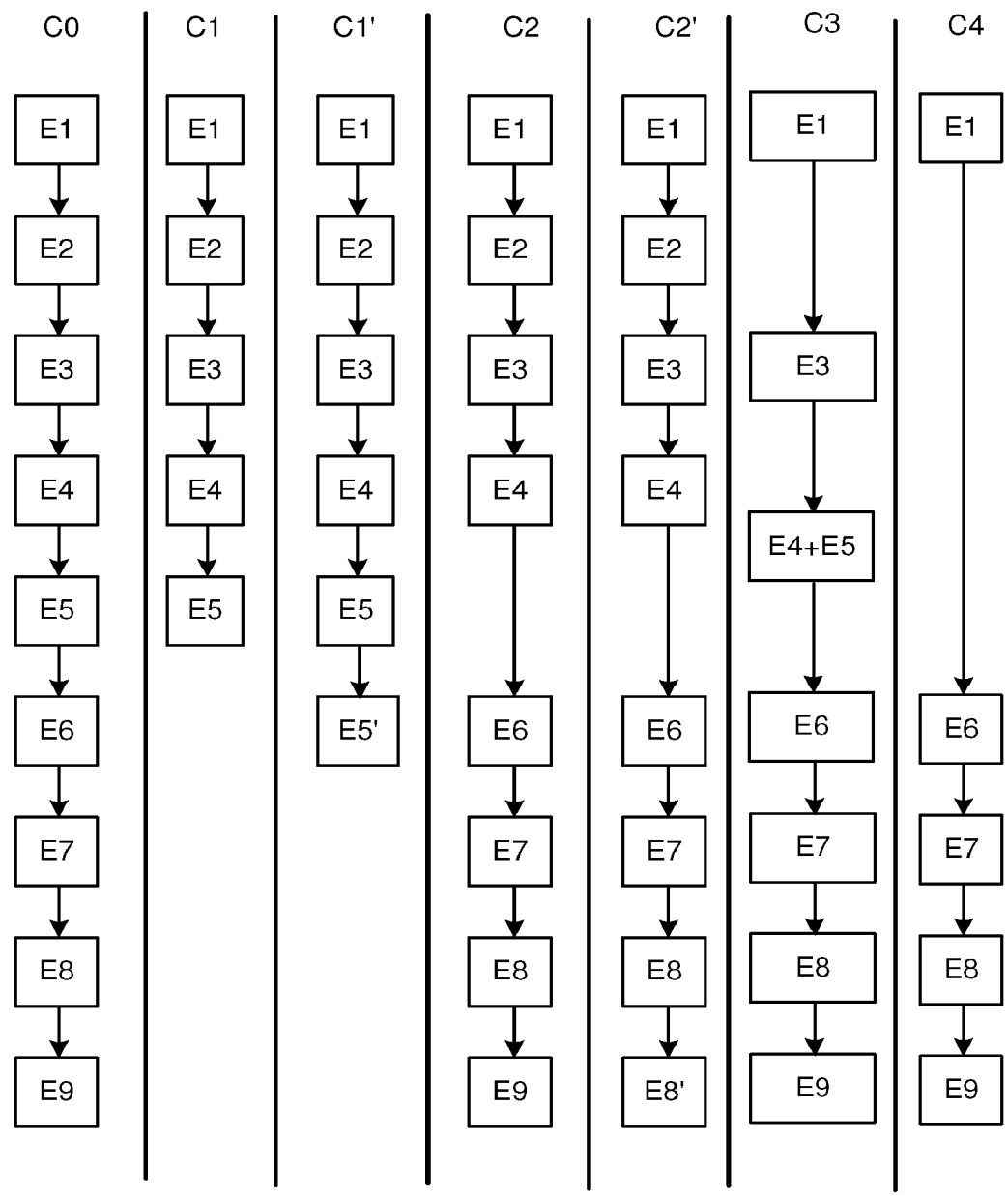
FIG. 1 illustrates the various possible configurations of a method for preparing and analyzing a sample containing biological species.

Referring to FIG. 1, the complete analysis (column C0) of a biological sample may comprise the following steps carried out successively:

E1: Concentrating the biological species present in the biological sample,
E2: Washing for purification, to remove the interfering substances in culture,
E3: Supplying a culture medium,
E4: Culturing the biological species,
E5: Visual monitoring of growth during culture, and colony counting,
E6: Washing, to remove the PCR inhibitors,
E7: Mechanical lysis of the biological species present in the sample with a view to extracting therefrom a biological material to be investigated,
E8: Separation between the biological material to be investigated and the contaminants present,
E9: Detecting the presence of pathogens in the biological material by biomolecular amplification of the qPCR, LAMP, RPA type and optical detection such as for example fluorescence, colorimetry, holographic imaging, turbidimetry, pH measurement in conjunction with the amplification reaction.

In the concentration step, the biological sample, for example in liquid form, comprising the biological species, is injected into a chamber for passing through a filter. The liquid part of the sample and all the particles/molecules that pass through the filter are recovered via an evacuation channel and removed from the analysis. The biological species are then concentrated in a space of the chamber.

A washing/rinsing solution may be injected for washing the biological species present in the chamber.

A culture medium is injected for culturing the biological species.

The growth monitoring step makes it possible, by optical reading, to monitor cell growth during the culture step.

Mechanical lysis of the biological species is employed for grinding the biological species present in the sample against a rough contact surface. Once mechanical lysis has been carried out, we have a biological material that is to be investigated, formed for example of DNA molecules and contaminants.

Separation between the biological material to be investigated and the contaminants is effected by injecting a liquid solution containing amplification reagents, for eluting the biological material to be investigated. A portion of the liquid solution injected thus carries the biological material to be investigated, for example the DNA molecules, which passes through the filter.

Once separation between the contaminants and the biological material to be investigated has been effected, the reaction of amplification of the biological material makes it possible to detect the presence of a pathogen in the biological material that has been separated. The amplification reaction is carried out by adding an amplification mixture and heating a chamber in which the sample has been placed. The temperature to which the chamber is heated depends on the type of amplification reaction employed. All types of amplification reaction are possible, for example LAMP ("Loop-Mediated Isothermal Amplification"), PCR ("Polymerase Chain Reaction"), NASBA ("Nucleic Acid Sequence Based Amplification"), RPA ("Recombinase Polymerase Amplification") etc. For an amplification of the LAMP type, heating is carried out at a temperature advantageously between 60° C. and 65° C. This reaction makes it possible to amplify the molecules of the biological material to be detected, for example the DNA molecules. In the reaction of amplification of the biological material, it is a matter of detecting whether a pathogen is present. Various methods may be employed for this, for example such as colorimetry, fluorescence, electrochemistry, pH measurement, measurement of turbidity. Any other method of detection could be envisaged. For a method of detection of the pH measurement type, the electrodes for detecting pH could be integrated in the device.

However, some of the above steps are optional, and the method of analysis may therefore assume various possible configurations.

In a first configuration C1 (FIG. 1), the method may comprise the following steps:
E1: Concentration,
E2: Washing,
E3: Supplying a culture medium,
E4: Culture E5: Visual monitoring of growth during culture, and colony counting, In a configuration C1' repeating steps E1 to E5 of the first configuration, a step E5' may be added after step E5 in order to collect bacteria for treatment.

In a second configuration C2 (FIG. 1), the method may comprise the following steps:
E1: Concentration,
E2: Washing,
E3: Supplying a culture medium,
E4: Culture,
E6: Washing,
E7: Lysis,
E8: Separation,
E9: Detection by amplification.

Moreover, in a configuration C2' repeating steps E1 to E8 of configuration C2, a step E8', replacing step E9, may be added. This step consists of bringing out again the DNA separated for detection/storage, notably with a view to DNA sequencing.

In a third configuration C3 (FIG. 1), the method may comprise the following steps:
E1: Concentration,
E3: Supplying a culture medium,
E4+E5: Culture/Monitoring growth,
E6: Washing,
E7: Lysis,
E8: Separation,
E9: Detection by amplification.

In a final configuration C4, it is also possible to omit steps E2 to E5. We thus have:
E1: Concentration,
E6: Washing, removal of the PCR inhibitors,
E7: Lysis,
E8: Separation,
E9: Detection by amplification.

In this configuration C4, a variant including step E8' is also conceivable, with a view to bringing out the released DNA again.

The invention aims to propose a microfluidic device whose architecture is adapted for implementing at least two of the configurations described above.

Figure 2A:
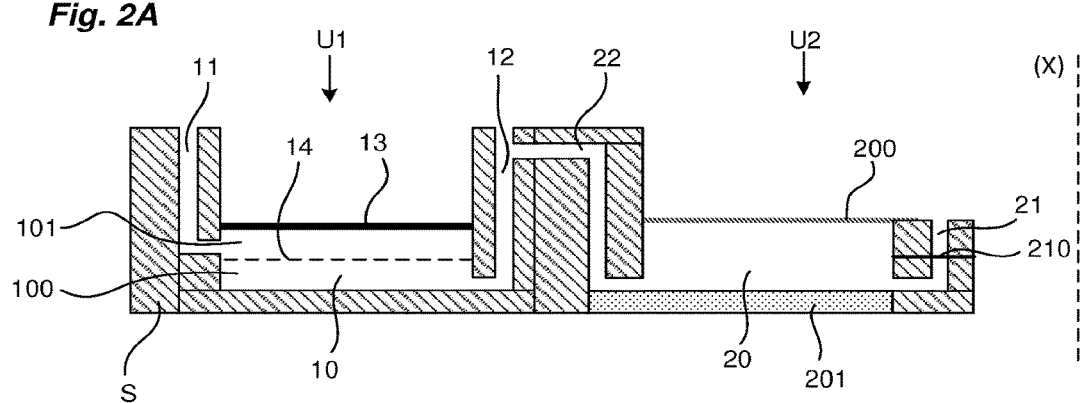
FIGS. 2A to 2C show three embodiments of the device of the invention.
Figure 2B:
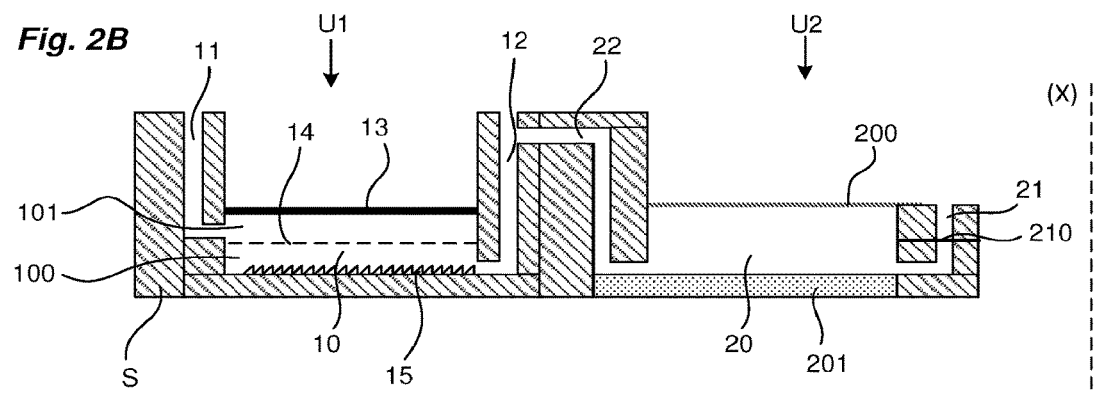
Figure 2C:
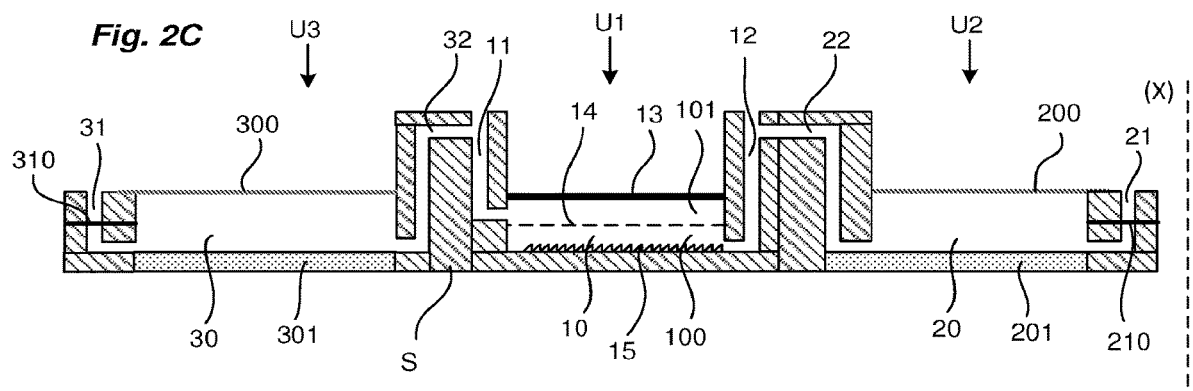
Figure 3A:
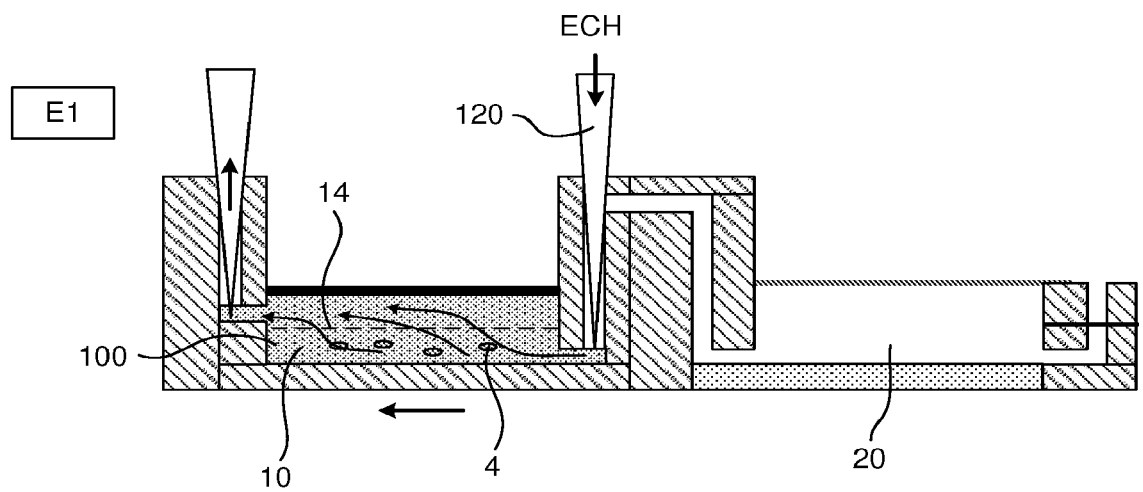
FIGS. 3A to 3D show the different steps of preparation and analysis carried out with the device in FIG. 2A.
Figure 3B:
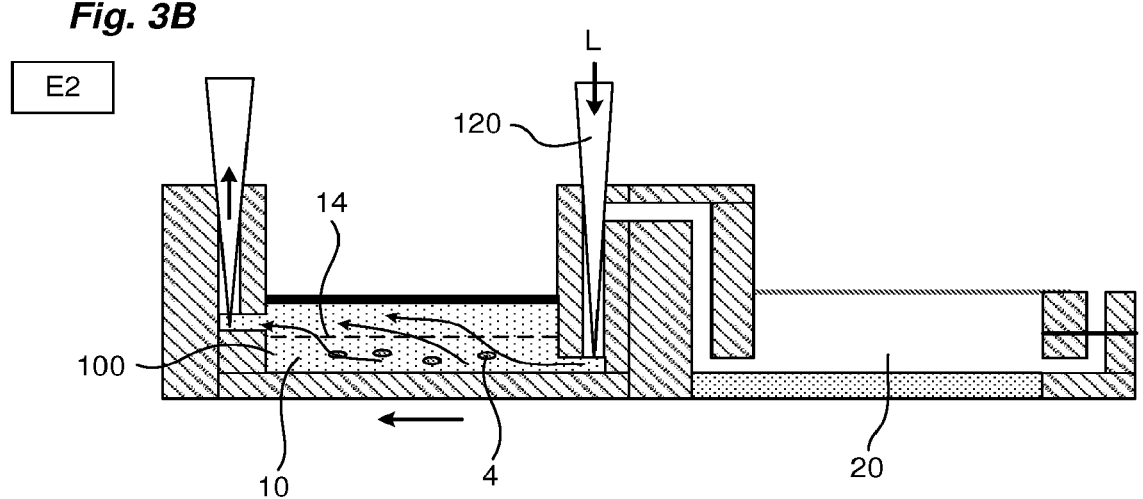
Figure 3C:
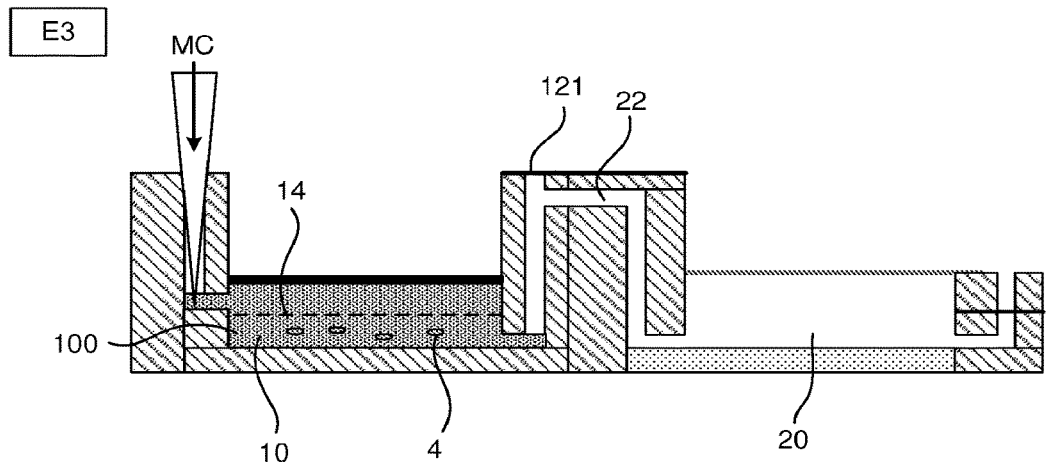
Figure 3C:
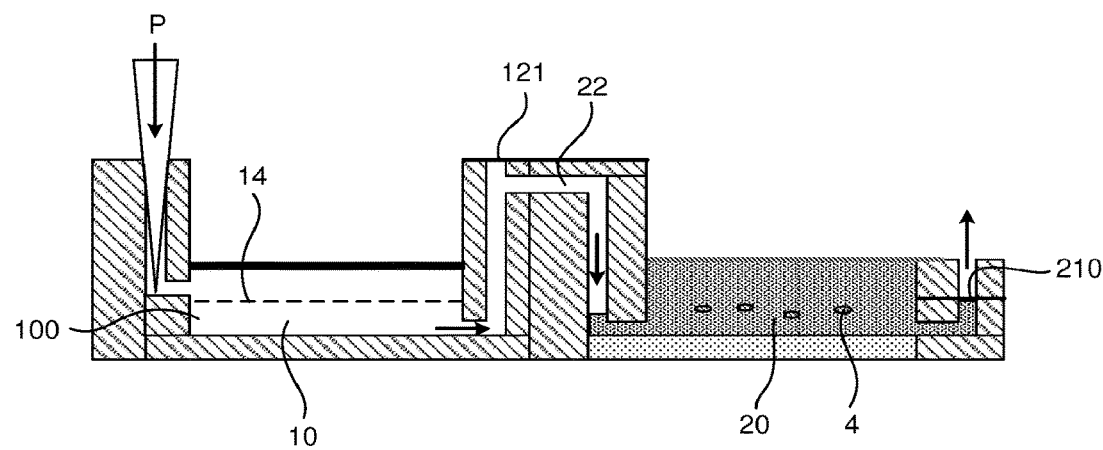
Figure 3D:
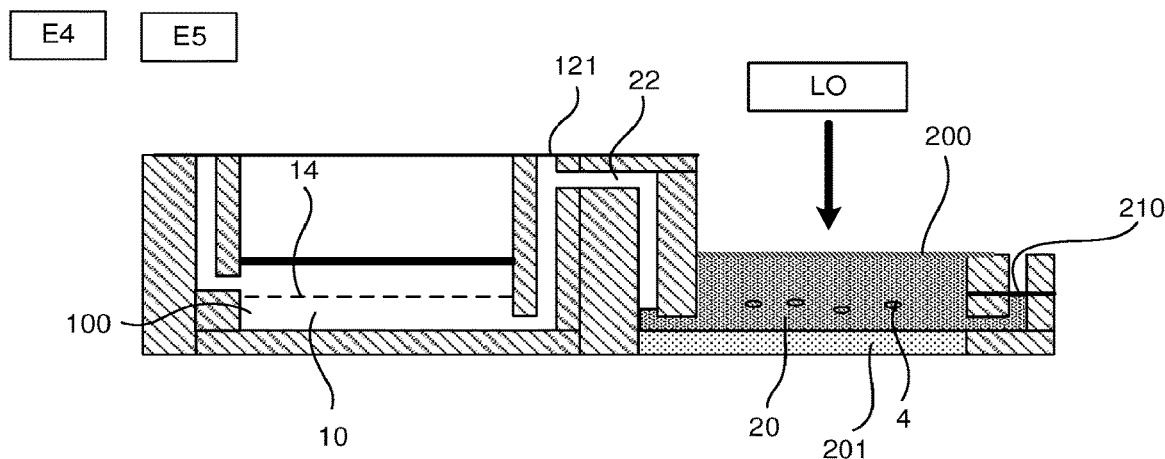
Figure 4A:
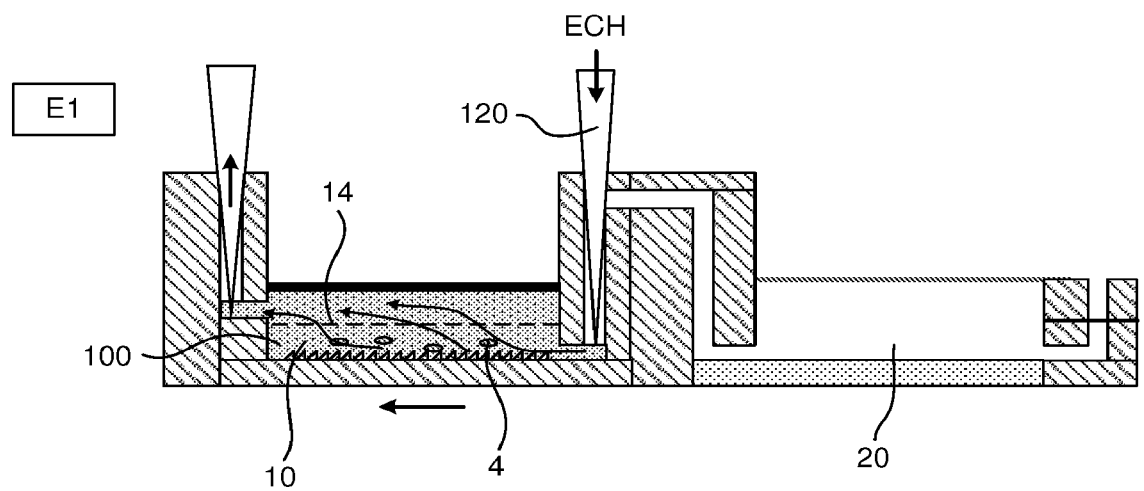
FIGS. 4A to 4H show the different steps of preparation and analysis carried out with the device in FIG. 2B.
Figure 4B:
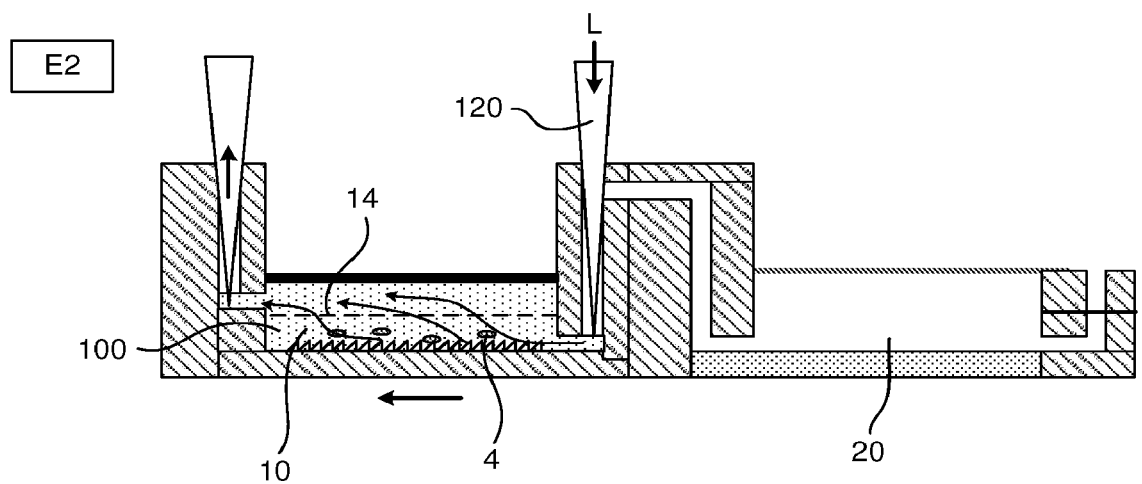
Figure 4C:
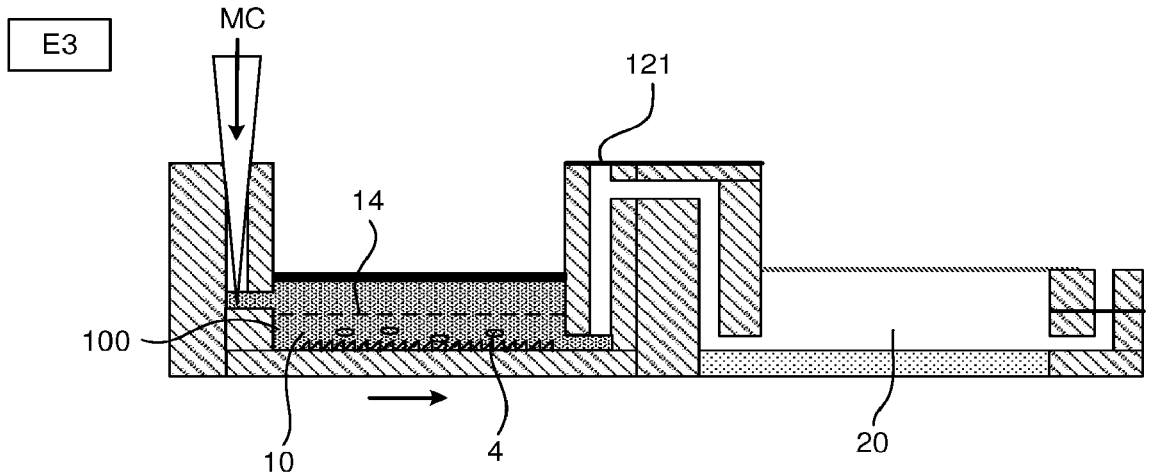
Figure 4D:
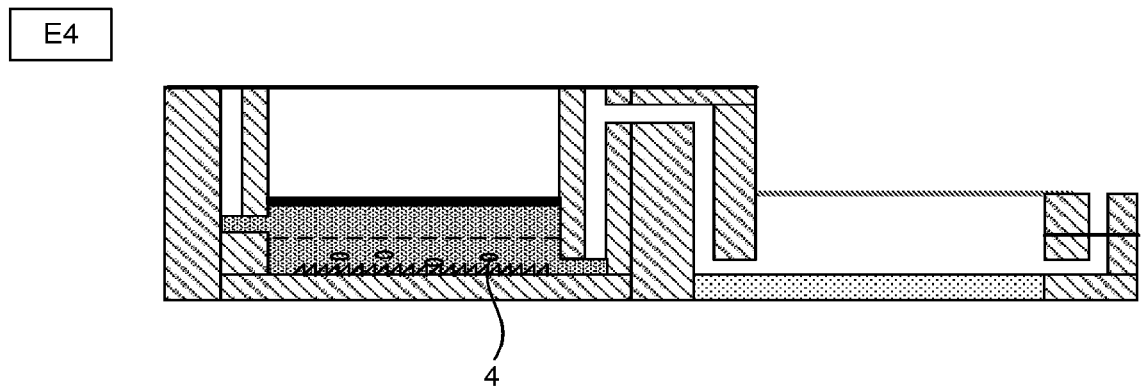
Figure 4E:
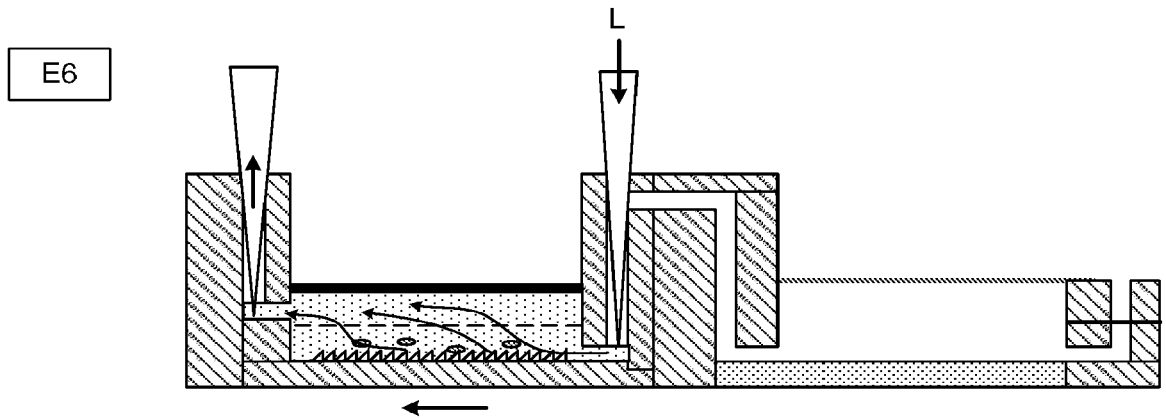
Figure 4F:
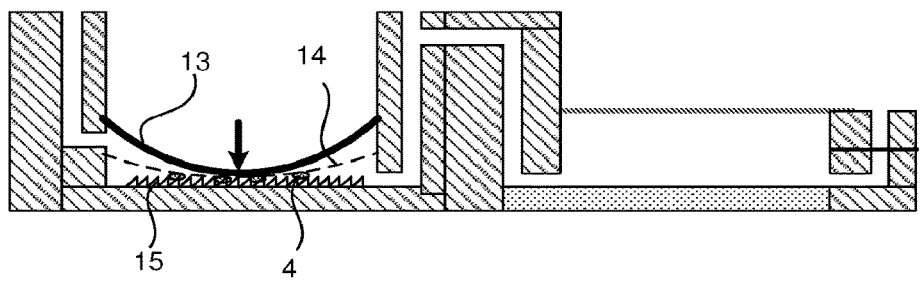
Figure 4G:
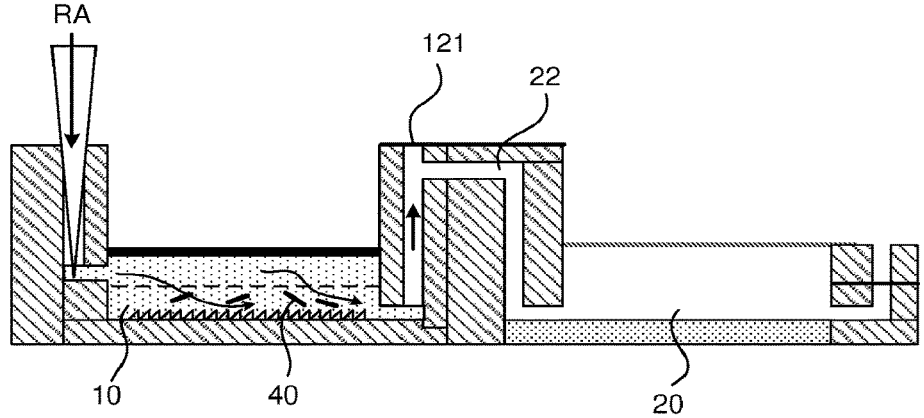
Figure 4G:
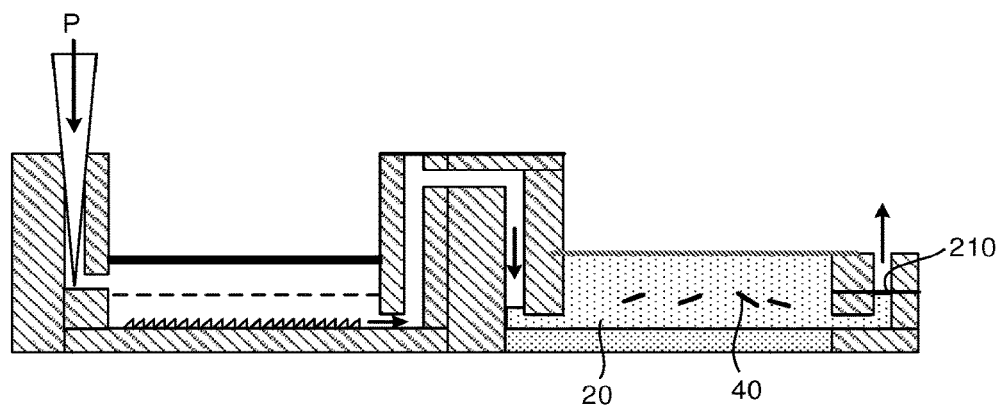
Figure 4H:
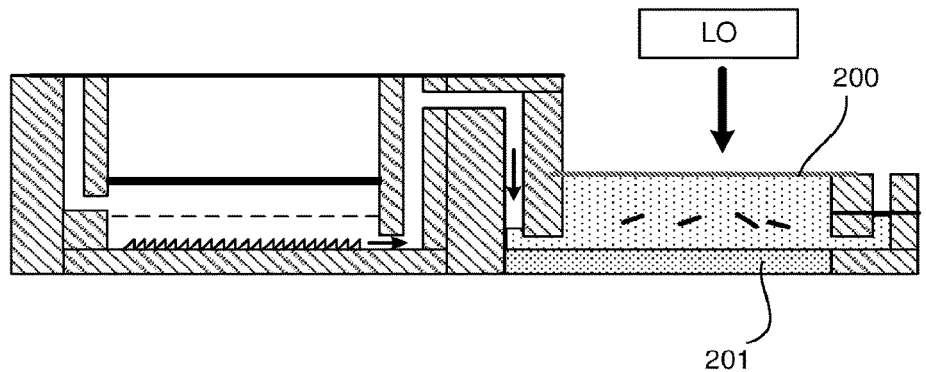
Figure 5C:
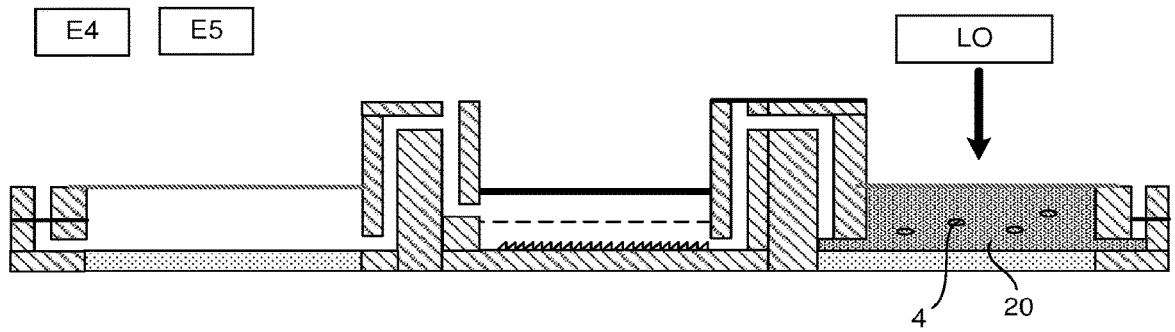
Figure 5D:
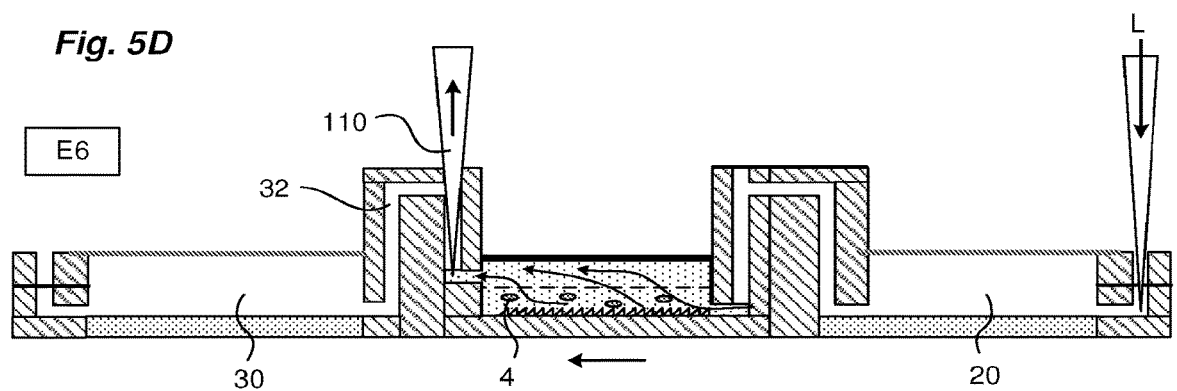
Figure 5D:
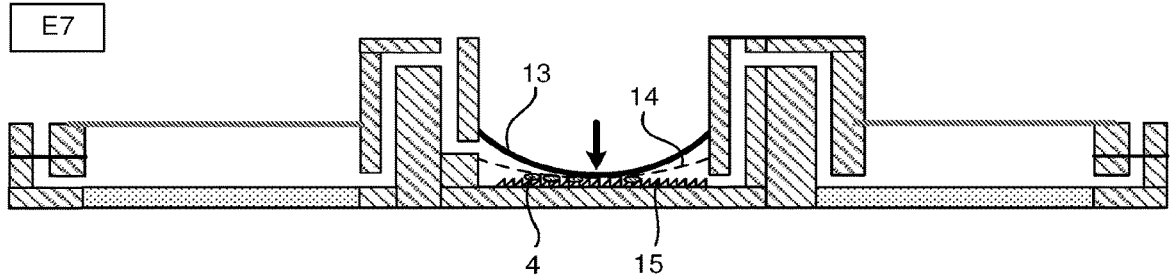
Figure 6:
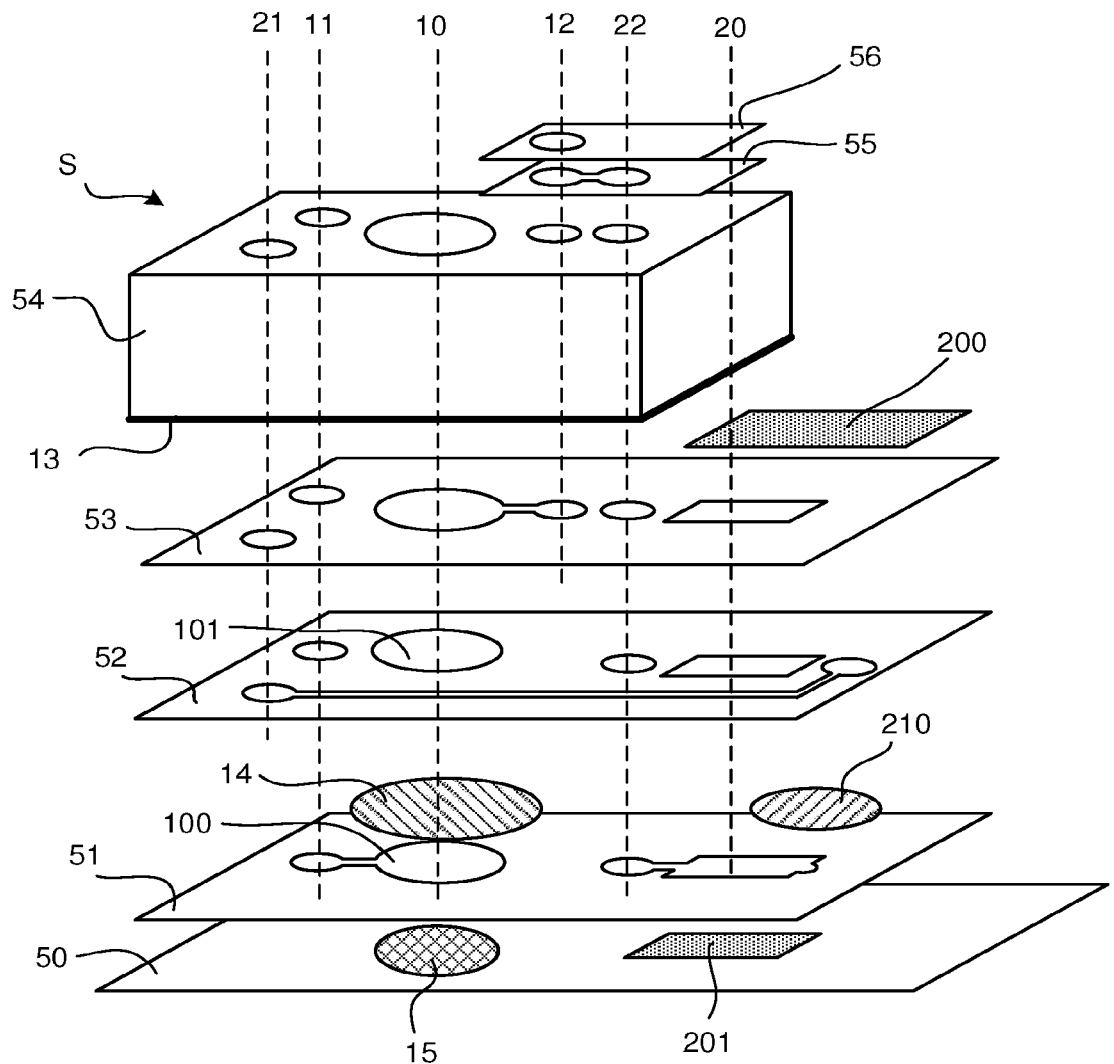
FIG. 6 shows, in an exploded view, an embodiment example of the device of the invention, in the variant in FIG. 2B.

Referring to FIGS. 2A to 2C, the microfluidic device comprises a single rigid support S. FIG. 6 described hereunder gives an embodiment example of the device.

This rigid support S incorporates a microfluidic network suitable for implementing the steps of the method of analysis. It will be seen that the microfluidic network may assume different architectures depending on the configuration of the method of analysis that is used.

The support S advantageously comprises a flat lower wall and an architecture with several superposed layers along said principal axis, stacked on its lower wall.

The microfluidic network of the device comprises two units U1, U2 or three units U1, U2, U3 each used for implementing one or more of the steps of the method of analysis, depending on the configuration of the method that is selected.

In the device of the invention, the biological species are cultured in a thin layer, i.e. with a volume that may range from 1 µl to 1 ml. The advantage of culturing in a thin layer is that the colonies may be visible much more quickly (duration of the order of 2 to 3 hours) than with a culture carried out in the conventional manner. By combining a step of concentration of the cells and thin-layer culture, it is thus possible to analyze samples with a very low charge of cells.

It will thus be possible for example to analyze large volumes of water, for the purpose of monitoring the level of contamination.

Moreover, owing to the device, it is possible to perform the entire step of purification of the DNA molecules and then their transfer to another chamber for amplification in its entirety, without a dilution step and without any risk of contamination.

In the three embodiments proposed and illustrated in FIGS. 2A to 2C, the first unit U1 comprises a first chamber 10 made in said support. This chamber 10 has a non-zero volume and is delimited by walls of the support S.

The first unit U1 comprises a first channel 11 made in the support for injecting fluids into the first chamber 10 or for evacuating fluids out of this first chamber. The first channel 11 comprises a first end comprising an opening made for example through an upper wall of the support S and a second end that opens into said first chamber 10. The first end of the first channel is for example arranged vertically and its second end opens for example horizontally into the first chamber 10.

The first unit U1 comprises a second channel 12. This second channel 12 also comprises a first end that communicates with the exterior, forming an opening made for example through an upper wall of the support S and a second end that communicates with the space formed by the first chamber 10. Via this second channel 12, it is also possible to inject fluids into said first chamber or evacuate fluids out of said first chamber. Its first end is for example arranged vertically and its second end horizontally. The first chamber 10 is placed between the first channel 11 and the second channel 12.

The top of the first chamber 10 may be closed by a flexible, stretchable membrane 13. At the level of the first chamber, an upper wall of the support thus comprises an opening that is covered hermetically by said membrane 13. The membrane 13 is thus anchored in the support by any suitable solution for fixation, for example by gluing. This membrane 13 will consist for example of a film, for example of the type MicroAmp, 3M (registered trademarks), with suitable thickness, dimensions and constitution for deforming hyperelastically, relative to its anchorage points, at least as far as the bottom of the first chamber.

The membrane 13 is able to deform reversibly between several configurations. It can stretch by hyperelastic deformation toward the exterior of the support S, retract to the interior of the first chamber 10 by compression, or can be at rest. "Hyperelastic material" means a material able to have a surface capable of changing from a first surface area to a second surface area, the second surface area being equal to at least 5 times the first surface area, for example 10 times or even 50 times the first surface area.

The first unit U1 also comprises a transverse filter 14 arranged in said first chamber 10 and separating said first chamber 10 into two spaces 100, 101. The two spaces are for example superposed and are thus designated lower space 100 located under the filter 14 and upper space 101 located above the filter 14. This filter 14 is preferably made wholly or partly in the form of a thin, flexible film, stretched out in the space formed by the chamber so as only to allow passage from one space to the other via the pores of the filter 14. The film has an elastic deformability that allows it to stretch on application of a supporting force in an approximately vertical direction, this elastic deformability being of a level sufficient to reach the bottom of the chamber 10. The filter 14 has an average pore diameter between 0.2 µm and 50 µm, for example between 0.2 µm and 1 µm for separating microorganisms. The pore diameter is of course adapted to ensure separation between different biological species present in the sample. The filter 14 will for example consist of a film of thickness, dimensions and constitution suitable for it to deform as far as the bottom of the chamber 10 relative to its anchorage points. It may comprise the same hyperelasticity characteristics as the membrane.

According to a particular feature, the first channel 11 opens into the upper space 101 of the first chamber 10 and the second channel 12 opens into the lower space 100 of the first chamber 10. The mouths of the two channels are therefore separated by the filter 14 arranged in the chamber.

Referring to FIGS. 2B and 2C, the first unit U1 may advantageously comprise a rough contact surface 15 arranged at the bottom of the first chamber 10. This rough contact surface 15 extends over a major part of the bottom of the first chamber. It comprises a parameter of average surface roughness between 0.1 μm and 10 μm, preferably between 0.2 μm and 3 μm. This rough contact surface 15 is intended to allow mechanical lysis of the biological species present in a biological sample placed in the device. Preferably, mechanical lysis is achieved by grinding said biological species, by abrasion on said rough contact surface. The grinding operation is carried out by a movement of friction of the biological species against the rough contact surface, using a suitable grinding member. This member will be for example a spatula or a rod, for example made of plastic or metal. This member is applied from outside the chamber 10 and its end is applied against the outside surface of the membrane 13 so as to stretch the membrane 13 and the filter 14 toward the bottom of the first chamber 10 and thus rub the biological species present in a sample against the rough contact surface 15.

For its part, the second unit U2 of the device comprises a second chamber 20 of nonzero volume, delimited by walls of the support S. The second unit U2 also comprises a third channel 21 made in said support. This third channel 21 comprises a first end comprising an opening made for example through an upper wall of the support and a second end that opens only into said second chamber 20. The first end of this third channel 21 is for example arranged vertically and its second end opens for example horizontally into the second chamber 20. The first end of this third channel is for example sealed by a hydrophobic membrane 210, i.e. which is impermeable to liquids but permeable to gases such as air. This hydrophobic membrane 210 may be made of a material of the PTFE (polytetrafluoroethylene) type.

Two transverse walls of the support, advantageously an upper wall 200 and a parallel lower wall 201, partially delimiting the second chamber 20, are made of a transparent material, thus making it possible to perform optical reading through the interior space of the second chamber. The term "transparent" means that the material used is at least partially transparent to visible light, so as to allow at least 80% of said light to pass through. It will thus be understood that it will be sufficiently transparent to see the interior of the chamber. The lower wall may be made of glass and the upper wall may be formed from a detachable adhesive glued to close said second chamber from the upper side.

According to a particular feature of the invention, the device also comprises a first transfer channel 22 made in said support. This first transfer channel 22 is intended to connect the first chamber 10, more precisely its lower space 100, to the second chamber 20.

Advantageously, the first transfer channel 22 comprises a first end opening directly into the second channel 12, thus forming a bypass node on this second channel 12. It comprises a second end opening directly into the second chamber.

The device further comprises switching means that may for example be arranged on the second channel 12 for selecting connection of the first chamber:
  to the exterior only, via the second channel only or,
  to the second chamber only, through the first transfer channel.

These switching means may consist of a detachable hollow cone 120 that is in the form of a funnel. When it is inserted by its vertex into the second channel 12, it allows communication between the exterior and the first chamber, and its wall blocks the entrance of the first transfer channel 22, made at the level of the bypass node. When it is removed, the first end of the second channel 12 may be sealed, for example using an adhesive 121 applied on a surface of the support, and the connection between the first transfer channel 22 and the second channel 12 is then open, allowing a fluid to circulate between the first chamber 10 and the second chamber 20.

Of course, the switching means may be configured according to other embodiments. The general principle is to be able to gain access to the first chamber by sealing the transfer channel or to allow connection between the first chamber and the second chamber. It may thus be a simple valve which:
  in a first position, makes it possible to authorize access to the second channel by sealing the mouth of transfer channel 22 at the level of the bypass node,
  in a second position, makes it possible to open the connection between the second channel 12 and the transfer channel 22.

In an architecture with only two units U1, U2 as described above, the method may be carried out according to the first configuration or the second configuration described above.

In the first configuration C1 of the method implemented in the device in FIG. 2A and referring to FIGS. 3A to 3D, the steps are then as follows:
  E1: The liquid sample ECH is injected via the second channel 12 for example by means of a pipette to the first chamber 10 through the cone 120. The cone 120 is arranged in the second channel at a sufficient depth to seal the entrance of the first transfer channel 22, at the level of the bypass node. At the same time, the first channel 11 is opened to the exterior to perform the role of vent during filling of the first chamber 10 and to evacuate the filtered liquid. During injection, under the effect of the injection pressure, the sample is filtered by the filter 14. The biological species 4 of interest are held in the lower space 100 of the first chamber 10 and the remainder is evacuated to the exterior of the device via the first channel 11.
  E2: In the same configuration, the washing step (optional) is then carried out. A washing liquid L is injected via the second channel 12, through the cone, to purify the biological species 4 captured in the lower space 100 of the first chamber 10. This washing liquid is evacuated through the first channel 11.
  E3: A culture medium MC is injected via the first channel 11 to penetrate into the first chamber 10. The inlet/outlet of the second channel 12 is closed by the adhesive 121 and the first transfer channel 22 is opened, allowing sealed communication, without risk of contamination, between the first chamber 10 and the second chamber 20.

E3: The biological species 4 in their culture medium MC are transferred to the second chamber 20 via the first transfer channel 22. For transfer, an air pressure P may be applied in the first channel 11. The third channel 21 is sealed due to the hydrophobic membrane 210, allowing the air to be evacuated during the transfer and preventing the liquid escaping. The culture step may take 16 hours, heating the second chamber 20 to a temperature of 37° C.

E4-E5: An optical reader LO is activated to monitor culture of the biological species present in the second chamber 20. Optical reading is enabled owing to the transparency of the two parallel walls 200, 201 delimiting the second chamber 20.

In the second configuration C2 of the method, implemented in the device in FIG. 2B, and referring to FIGS. 4A to 4H, the steps are then as follows:

E1: The liquid sample ECH is injected via the second channel 12 for example by means of a pipette to the first chamber 10 through the cone 120. The cone is arranged in the second channel 12 at a sufficient depth to seal the entrance of the first transfer channel 21, at the level of the bypass node. At the same time, the first channel 11 is opened to the exterior to perform the role of vent during filling of the first chamber 10 and to evacuate the filtered liquid. During injection, under the effect of the injection pressure, the sample ECH is filtered by the filter 14. The biological species 4 of interest are held in the lower space 100 of the first chamber 10 and the remainder is evacuated to the exterior via the first channel 11.

E2: The washing step (optional) is then carried out. A washing liquid L is injected via the second channel 12, through cone 120, to purify the biological species 4 captured in the lower space 100 of the first chamber 10. This washing liquid L is evacuated to the exterior through the first channel 11.

E3: A culture medium MC is injected via the first channel 11 to penetrate into the first chamber 10.

E4: Culture is carried out in the first chamber 10. The culture step may take 4 hours, heating the first chamber 10 to a temperature of 37° C.

E6: A washing liquid L is injected via the second channel to wash the biological species present in the lower space of the first chamber.

E7: Lysis of the biological species 4 is carried out in the first chamber. This lysis consists of grinding the biological species 4 against the rough contact surface 15 present at the bottom of the first chamber 10.

E8: The transfer channel 22 between the two chambers is opened. An amplification reagent RA is injected via the first channel 11 to carry out elution of the biological material 40 obtained after lysis and transfer the liquid of interest to the second chamber 20, via the transfer channel 22.

A pressure P may be applied through the first channel 11 to effect transfer of the liquid of interest to the second chamber 20.

An amplification reaction is carried out in the second chamber for 45 minutes, heating the second chamber to a temperature of 60° C. An optical reader LO is activated to perform detection of pathogens in the second chamber 20. Optical reading is enabled owing to the transparency of the two parallel walls 200, 201 delimiting the second chamber.

Referring to FIG. 2C, the device may advantageously comprise a third unit U3, allowing it to carry out the method according to the third configuration C3 described above. The third unit U3 comprises a third chamber 30 of nonzero volume, integrated with said support S. The third unit U3 comprises a fourth channel 31 made in the support S for injecting fluids into the third chamber 30 or for evacuating fluids out of this third chamber 30. The fourth channel 31 comprises a first end having an opening made for example through an upper wall 12 of the support and a second end that opens into said third chamber 30. The first end of the first channel 31 is for example arranged vertically and its second end opens for example horizontally into the third chamber 30. The first end of this fourth channel 31 is for example sealed by a hydrophobic membrane 310, i.e. impermeable to liquids but permeable to gases such as air. This hydrophobic membrane may be made of a material of the PTFE (polytetrafluoroethylene) type.

Two walls of the support, advantageously an upper wall 300 and a lower wall 301, delimiting the third chamber 30, are made of a transparent material, thus making it possible to perform optical reading through this third chamber. The term "transparent" means that the material used is at least partially transparent to visible light, so as to allow at least 80% of this light to pass through. It is thus to be understood that it will be sufficiently transparent to see the interior of the chamber. The lower wall may be made of glass and the upper wall may be formed from a detachable adhesive glued to close said third chamber from the upper side.

According to a particular feature of the invention, in this variant in FIG. 2C, the device also comprises a second transfer channel 32 made in said support S. This second transfer channel 32 is intended to connect the first chamber 10, more precisely its upper space 101, to the third chamber 30.

Advantageously, the second transfer channel 32 comprises a first end opening directly into the first channel 11, thus forming a bypass node on this first channel 11 (symmetrically to the first transfer channel). It comprises a second end opening directly into the third chamber 30.

Just as for the first transfer channel, the device further comprises switching means that may for example be arranged on the first channel 11 for selecting connection of the first chamber:
 to the exterior only via the first channel or,
 to the third chamber only through the second transfer channel.

These switching means may also consist of a detachable hollow cone 110 that is in the form of a funnel. When it is inserted in the first channel 11, it allows communication between the exterior and the first chamber 10 and its wall blocks the entrance of the second transfer channel 32, effected at the level of the bypass node. When it is withdrawn, the first end of the first channel 12 is sealed, for example using an adhesive 111 applied on a surface of the support, and the connection between the second transfer channel 32 and the first channel 11 is then open, allowing a fluid to circulate between the first chamber 10 and the third chamber 30.

Just as for the first switching means, it is to be understood that other means may be employed, the objective being to provide a solution for accessing the first chamber, by sealing the second transfer channel or to allow connection of the first chamber to the third chamber, through the second transfer channel. The switching means of the two-position valve type, described above, may be used identically.

In the third configuration C3 of the method implemented in the device in FIG. 2C and referring to FIGS. 5A to 5F, the steps are then as follows:

E1: The liquid sample ECH is injected via the second channel 12, for example using a pipette through the cone 120 to the first chamber 10. The cone 120 is arranged in the second channel 12 at a sufficient depth to seal the entrance of the first transfer channel 22, at the level of the bypass node. At the same time, the first channel 11 is opened to the exterior to perform the role of vent during filling of the first chamber 10 and to evacuate the filtered liquid. During injection, under the effect of the injection pressure, the sample ECH is filtered by the filter 14. The biological species 4 of interest are held in the lower space 100 of the first chamber 10 and the remainder is evacuated to the exterior via the first channel 11.

The washing step (optional, not shown) is then carried out. A washing liquid is injected via the second channel, through the cone, to purify the biological species captured in the lower space of the first chamber. This washing liquid is evacuated through the first channel.

E3: A culture medium MC is injected via the first channel 11 to penetrate into the first chamber 10. The inlet/outlet of the second channel 12 is closed by the adhesive 121 and the first transfer channel 22 is open, allowing sealed communication, without risk of contamination, between the first chamber 10 and the second chamber 20.

E3: The biological species 4 in their culture medium MC are transferred to the second chamber 20 via the first transfer channel 22. For transfer, an air pressure P may be applied in the first channel. The third channel 21 is sealed due to the hydrophobic membrane 210, allowing the air to be evacuated during the transfer and preventing the liquid escaping.

E4-E5: The culture step may take 4 hours, heating the first chamber to a temperature of 37° C. Optical monitoring of the culture is carried out through the second chamber 20, using an optical reader LO. This first reading step makes it possible to ensure that the culture is effective. As an example, if in the case of a sterility test, no bacterium is detected in culture in the second chamber 20, it is pointless to continue the procedure and perform purification and amplification of the bacterial DNA. This approach makes it possible to minimize the total cost of the analysis.

E6: If the analysis is continued, a washing liquid L is injected via the third channel 21 to wash the biological species 4 present in the second chamber 20 and transfer the sample to the first chamber 10, through the first transfer channel 22. The cone 110 is in place to close the access to the third chamber 30 via the second transfer channel 32.

E7: Lysis of the biological species 4 is carried out in the first chamber 10. This lysis consists of grinding the biological species 4 against the rough contact surface 15 present at the bottom of the first chamber 10.

E8: The second transfer channel 32 is opened. An amplification reagent RA is injected via the second channel 12 for carrying out elution of the biological material obtained after lysis and to transfer the liquid of interest from the first chamber 10 to the third chamber 30.

A pressure P may be applied through the second channel to effect transfer of the liquid of interest to the third chamber.

An amplification reaction is carried out in the third chamber for 45 minutes, heating the second chamber to a temperature of 60° C. An optical reader is activated to perform detection of pathogens in the third chamber. Optical reading is enabled owing to the transparency of the two parallel walls delimiting the third chamber.

The versatility of the device of the invention is better understood, whether it is in its architecture with two units U1, U2 or with three units U1, U2, U3.

To summarize:

In the first configuration C1 of the method or in configuration C1', the first unit U1 may be used for steps E1, E2 and E3 and the second unit U2 for steps E4 and E5.

In the second configuration C2 of the method or in configuration C2', the first unit U1 may be used for steps E1, E2, E3, E4, E6, E7 and E8 and the second unit U2 for step E9.

In the third configuration C3 of the method, the first unit U1 may be used for steps E1, E3, E6, E7 and E8, the second unit U2 for steps E4 and E5 and the third unit for step E9.

In configuration C4 of the method, the first unit U1 may be used for steps E1, E6, E7, E8 and the second unit for step E9.

The two transfer channels make it possible to pass easily from one unit to another, while avoiding contamination.

The device may advantageously incorporate means for heating the internal space of each chamber, consisting for example of at least one heating resistance 19 or a Peltier element, as shown in the appended figures. The resistance is for example fixed under the lower wall of the casing. A power source 20 will for example be provided for supplying the resistance 19. The power source will comprise for example one or more electric cells, supplying enough energy to heat the chamber to a temperature in the range defined above, i.e. from 20° C. to 100° C. Of course, other heating means could be used, comprising for example a conductive ink deposited by printing or screen printing under the lower wall of the casing. These heating means are used for heating the chamber to a given temperature during a step of culture of the biological species or during an amplification reaction.

In a nonlimiting manner, in its variant in FIG. 2B, the device may be made according to the architecture shown in FIG. 6.

In FIG. 6, the support S comprises the following particular features:

The support comprises a lamina 50, for example of glass or of plastic, of the PMMA or COC type;

The lamina 50 is covered in a first zone with an abrasive surface so as to form, on a portion of its upper face, the rough contact surface 15 dedicated for lysis;

In at least one second zone, the lamina 50 is transparent to form the transparent lower wall 201 of the second chamber 20, intended for optical reading;

A first layer 51 bearing a first microfluidic imprint is deposited on the upper face of the lamina 50, this first imprint comprising a first cavity defining the lower space 100 of the first chamber 10, a second cavity defining a lower portion of the second chamber 20 and the lower portion of the third channel 21; the first cavity has its edges arranged around the first abrasive zone and the second cavity has its edges arranged around the second reading zone;

The filter 14 is affixed on the first layer to cover the lower space 100 of the first chamber and the hydrophobic membrane 210 is affixed on the lower portion of the third channel 21;

A second layer 52 bearing a second microfluidic imprint is deposited on the upper face of the first layer 51, also covering the filter 14 and the hydrophobic membrane 210. This second microfluidic imprint comprises a cavity forming the upper space 101 of the first chamber 10, a second cavity forming a middle portion of the second chamber 20 and the upper portion of the third channel 21;

A third layer 53 bearing a third microfluidic imprint is deposited on the upper face of the second layer 52; this third microfluidic imprint comprises the upper portion of the first chamber 10 and the upper portion of the second chamber 20;

A glass or plastic lamina is dimensioned to cover the upper face of the third layer 53 at the level of the second chamber, forming the transparent upper wall 200 of the support;

A cover 54, for example of PMMA, is positioned above the first chamber 10; on its lower face, the cover comprises the membrane 13 that is intended to close the first chamber from above;

The cover comprises an upper axial opening, allowing access to the membrane 13, for carrying out lysis;

The cover 54 comprises two fluidic inlets/outlets on its upper face. The first inlet/outlet is connected to a first axial through channel formed through the membrane 13 and the three layers and opening into the first chamber 10 to form the first channel 11 of the support; the second inlet/outlet is connected to a second axial through channel formed through the membrane 13 and the second and third layers and opening out above the hydrophobic membrane 210, to form the third channel 21 of the support;

The support finally comprises two other through channels forming the first transfer channel 22 connecting together the two chambers 10, 20;

Two other layers 55, 56 make it possible to form the inlet of the second channel 12 and the junction of the transfer channel 22 on this second channel 12.

In the variant with three chambers in FIG. 2C, the architecture of the support would be similar, the principles for design of the third chamber 30 and of the second transfer channel 32 being modeled on those of the second chamber 20 and of the first transfer channel 22.

Advantageously, the second chamber 20 in the variant with only two units (FIGS. 2A and 2B) and the second chamber 20 and/or third chamber 30 in the variant with three units (FIG. 2C), have a suitably shaped internal volume, either for ensuring reliable control of the amplification reaction, or for identifying several targets simultaneously. In the latter case, the chamber may be shaped to allow several targets to be identified simultaneously. These assays, called multiplex, are used for example for detecting groups of pathogenic organisms corresponding to similar clinical symptoms or for detecting a bacterium but also its potential antibiotic resistance genes.

In the rest of the description, the architecture of a so-called amplification chamber 25 will be described in a general way. This architecture may be applied to the second chamber 20 and/or to the third chamber 30 of the device of the invention already described above.

This amplification chamber was designed to meet several objectives:
Optimize the fluidics (absence of bubbles);
Push the air out of the component but retain the liquid;
Not contaminate the environment;
Allow multiplexing;
Accommodate internal reaction control;
Limit the dead volumes;
Not split the sample.

The principle is to create at least one recess Ax (x ranging from 1 to N, N corresponding to the number of recesses and being greater than or equal to 1) in the amplification chamber, for housing a compound for internal reaction control (for example a selected DNA sequence or amplification primers targeting a predefined DNA) adapted to the amplification technology employed (PCR, LAMP RPA etc.). According to this principle, either the DNA is dried in the recess, in which case the primers are supplied by the liquid introduced via the chamber, or the primers are dried in the recess and the DNA is brought in by the liquid introduced into the chamber.

In the case of internal reaction control, the internal control compound may be deposited in the recess Ax at a known concentration and then dried directly in the chamber. It thus remains permanently in the device and is ready for use.

The advantage of depositing the control compound not directly in the optical reading zone but outside the latter is that in addition it makes it possible to optimize the space for gas exchange, and differentiate control amplification from target amplification. Control amplification will in effect be shifted both temporally and spatially.

Figure 7:
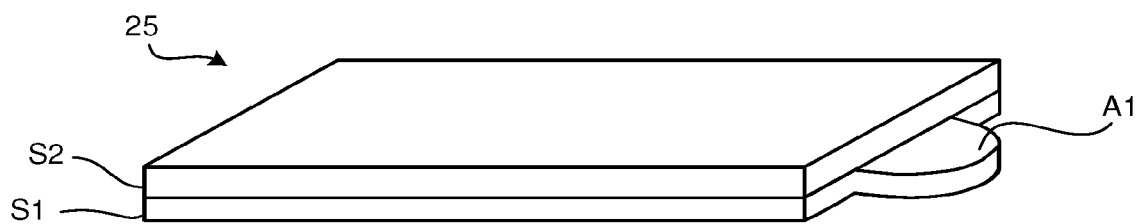
FIG. 7 shows an example of an amplification chamber that may be used in the device of the invention.

The architecture of the multilayer device makes it possible to construct the amplification chamber with strata of different designs. The lower stratum may in fact comprise one or more recesses and the upper strata of the chamber define the total optical reading cross section of the chamber. This principle with several strata is illustrated in FIG. 7. FIG. 7 shows a lower stratum S1 bearing the recess A1 and an upper stratum S2 defining the optical reading cross section (shown here nonlimitatively with a rectangular shape). The recess A1 in this case has a half-moon shape. It will be understood from this principle that the liquid penetrates into the whole chamber and that it can spread throughout the volume defined by the several strata, making it possible to avoid disturbing optical reading and to obtain the spatial and temporal shift described above.

Figure 8A:
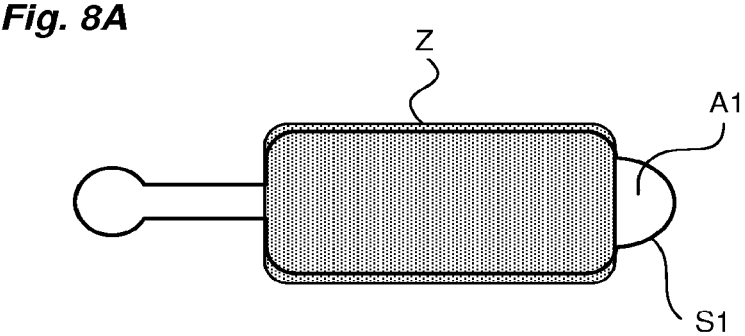
FIGS. 8A to 8C show several embodiments of the lower stratum of the amplification chamber, usable in the device of the invention.
Figure 8B:
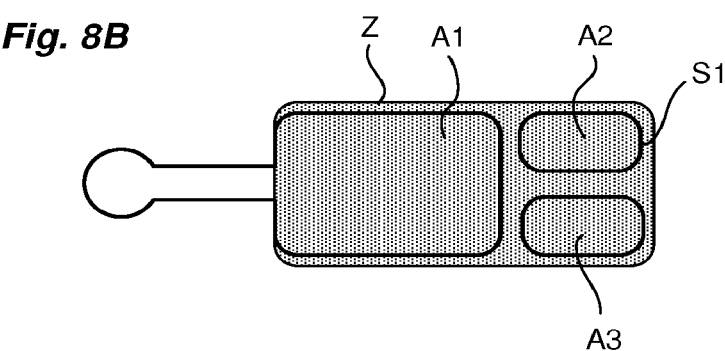
Figure 8C:
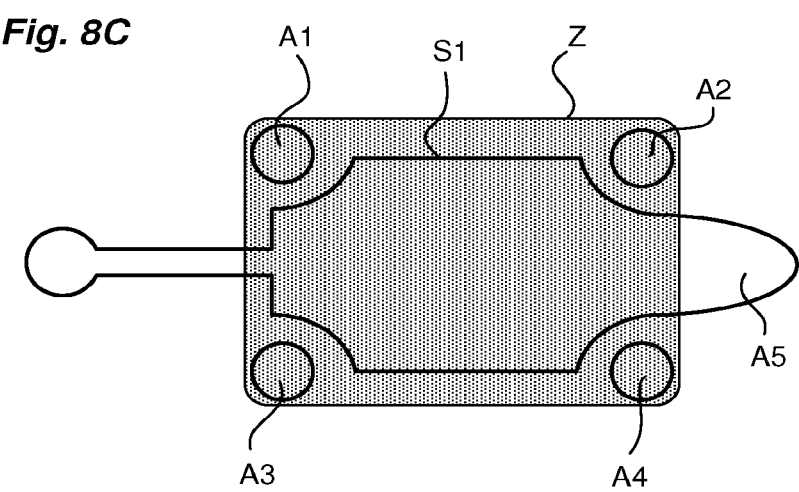

FIGS. 8A to 8C show different architectures of the stratum of the amplification chamber. In these figures, the optical reading zone Z is shown in gray. In FIG. 8A, the lower stratum S1 comprises a protuberance forming the recess A1 going beyond the section of the optical reading zone Z of the chamber in the transverse plane, opposite the point where liquid enters the chamber (corresponding to the design in FIG. 7). This offset zone makes it possible to shift the amplification reaction temporally and spatially. In FIG. 8B, the lower stratum S1 comprises three separate recesses A1, A2, A3 for housing three different primers. These three zones are located in the optical reading zone Z and allow the multiplexing principle to be employed. FIG. 8C shows a lower stratum, defining five separate zones, four recesses A1-A4 each made in the form of a cavity and a main zone comprising a protuberance having a fifth recess A5. The stratum of the chamber that is located just above defines the optical reading zone. The optical reading zone Z has a design covering the four recesses A1-A4 so that its volume is in fluid communication with the latter. The fifth recess may be outside the optical reading zone Z, as in the design in FIG. 8A.

As described above, each primer may be put in a separate recess of the chamber, in dry form. To facilitate drying it is recommended to take up the primers in an acid buffer (about pH 6) and facilitate their bonding to the glass of the lamina. It is also possible to use sugars (for example trehalose) to limit diffusion of the drop and potentially increase the stability of the dried DNA sequence.

It will be understood from the above elements that the device of the invention offers many advantages, including:
versatility that allows it to carry out reliably certain steps of the method for preparing and analyzing a biological sample or all the steps of said method;
a device that can be transported and manipulated easily;
an integrated device, allowing all the steps to be carried out in a single microfluidic support, without sample transfer and therefore without risk of contamination;
a device that offers a solution for reaction control, owing to the particular design of its amplification chamber.

The invention claimed is:

1. A microfluidic device for preparing and analyzing a biological sample containing biological species, said device comprising:
a single rigid support,
a first unit comprising a first chamber of nonzero volume delimited by walls of the support, a filter separating said first chamber into a first space and a second space, a first channel made in said support opening at one end onto a surface of said support and at another end into said first space and a second channel made in said support and opening at one end onto a surface of said support and at another end into said second space, and
a second unit comprising a second chamber made in said rigid support and delimited at least partially by a transparent wall of said support, a third channel made in said support and opening at one end onto a surface of said support and at another end into said second chamber,
wherein the device further comprises:
a first fluidic transfer channel between the first chamber and the second chamber, made in said support and having a first end opening into said second chamber and a second end at a first bypass node in said second channel, and
first flow switching means arranged for selecting connection of the first chamber:
to the exterior only, via the second channel only or,
to the second chamber only, through the first transfer channel.

2. The device according to claim 1, wherein the first unit comprises a rough contact surface made at a bottom of its first chamber.

3. The device according to claim 1, wherein the first chamber is closed by a deformable membrane.

4. A method for preparing and analyzing a biological sample containing a biological species, comprising:
providing the microfluidic device according to claim 3, and
carrying out, using the first unit, one or more of the following steps:
concentrating the biological species present in the biological sample,
washing to purify the biological species,
receiving a culture medium,
culturing the biological species,
lysis of the biological species in order to release a biological material, and
separating the biological material.

5. A method for preparing and analyzing a biological sample containing a biological species, comprising:
of providing the microfluidic device according to claim 3,
separating the biological material, and
carrying out, using the second unit, one or more of the following steps:
culturing the biological species,
visual monitoring of growth during said culture step, and
detecting a presence of pathogens in the separated biological material, by biomolecular amplification.

6. The device according to claim 1, further comprising a first hydrophobic membrane sealing the third channel.

7. The device according to claim 1, further comprising:
a third unit comprising a third chamber made in said rigid support and delimited at least partially by a transparent wall of said support, a fourth channel made in said support and opening at one end onto a surface of said support and at another end into said third chamber.

8. The device according to claim 7, further comprising:
a second fluidic transfer channel between the first chamber and the third chamber, made in said support and having a third end opening into said third chamber and a fourth end at a second bypass node into said first channel.

9. The device according to claim 8, further comprising second flow switching means arranged for selecting connection of the first chamber:
to the exterior only via the first channel only or,
to the third chamber only through the second transfer channel.

10. A method for preparing and analyzing a biological sample containing a biological species, comprising:
providing the device according to claim 9,
separating the biological material, and
carrying out, using the third unit, the following step:
detecting a presence of pathogens in the separated biological material, by biomolecular amplification.

11. The device according to claim 7, further comprising a second hydrophobic membrane sealing the fourth channel.

12. A method for preparing and analyzing a biological sample containing biological species, comprising:
providing the microfluidic device according to claim 7,
carrying out, using the first unit, one or more of the following steps:
concentrating the biological species present in the biological sample,
washing to purify the biological species,
receiving a culture medium,
culturing the biological species,
lysis of the biological species in order to release a biological material, and separating the biological material,
carrying out using the second unit one or more of the following steps:
culturing the biological species,
visual monitoring of growth during said culture step, and
detecting a presence of pathogens in the separated biological material, by biomolecular amplification, and
carrying out using the third unit the following step:
detecting the presence of pathogens in the separated biological material, by biomolecular amplification.

13. The device according to claim 1, wherein the second chamber comprises at least one recess configured to receive a compound for internal reaction control.

14. The device according to claim 13, wherein the second chamber is made up of several superposed strata and said recess is made in one of said strata only.

* * * * *